United States Patent [19]

Cooke et al.

[11] B 3,997,564

[45] Dec. 14, 1976

[54] N-(3,4-METHYLENEDIOXY-PHENYL)-UREAS

[75] Inventors: George A. Cooke, Denville; William J. Houlihan, Mountain Lakes, both of N.J.

[73] Assignee: Sandoz, Inc., E. Hanover, N.J.

[22] Filed: Sept. 11, 1974

[21] Appl. No.: 504,877

[44] Published under the second Trial Voluntary Protest Program on February 24, 1976 as document No. B 504,877.

Related U.S. Application Data

[60] Division of Ser. No. 351,093, April 13, 1973, Pat. No. 3,856,960, which is a division of Ser. No. 141,010, May 6, 1971, Pat. No. 3,748,331, which is a continuation-in-part of Ser. No. 34,902, May 5, 1970, abandoned, which is a continuation-in-part of Ser. No. 881,325, Dec. 1, 1969, abandoned.

[52] U.S. Cl. .......................................... 260/340.5
[51] Int. Cl.$^2$ ...................................... C07D 317/68
[58] Field of Search .................................. 260/340.5

[56] References Cited

UNITED STATES PATENTS 3,496,179  2/1970  Hess ............................. 260/340.5

OTHER PUBLICATIONS

Sandoz Ltd., Chemical Abstracts, vol. 64, 16550h to 16551a, (1966).

*Primary Examiner*—Richard L. Raymond
*Attorney, Agent, or Firm*—Gerald D. Sharkin; Richard E. Vila

[57] ABSTRACT

Disclosed are compounds of the class of 1-alkyl-4-phenyl and 4-(2-thienyl)-6,7-methylenedioxy-2(1H)-quinazolinones and quinazolinthiones, including the 3,4-dihydro derivatives thereof, useful as pharmaceutical agents, e.g. as anti-inflammatory agents. Such compounds, e.g. 1-isopropyl-4-phenyl-6,7-methylenedioxy-2(1H)-quinazolinones and 1-isopropyl-4-phenyl-6,7-methylenedioxy-2(1H)-quinazolinthiones, may be prepared by reacting the corresponding N-alkyl-N-(3,4-methylenedioxyphenyl)urea or thiourea with an aromatic aldehyde, e.g. benzaldehyde, in the presence of an acid at elevated temperatures to obtain the 3,4-dihydro-2(1H)-quinazolinones or 3,4-dihydro-2(1H)-quinazolinthiones which may then be oxidized to the corresponding 3,4-unsaturated compounds.

4 Claims, No Drawings

N-(3,4-METHYLENEDIOXY-PHENYL)UREAS

This application is a divisional of our earlier filed pending application Ser. No. 351,093, filed Apr. 13, 1973, now U.S. Pat. No. 3,856,960, which is a divisional of Ser. No. 141,010, filed May 6, 1971, now U.S. Pat. No. 3,748,331, which is a continuation-in-part of Ser. No. 34,902, filed May 5, 1970, now abandoned, which is a continuation-in-part of Ser. No. 881,325, filed Dec. 1, 1969, now abandoned.

This invention relates to cyclic compounds, and more particularly to 1-substituted-4-cyclosubstituted-methylenedioxy-2(H)-quinazolinones and quinazolinthiones having the methylenedioxy fraction joined at adjacent positions in the benzene portion of the quinazolinyl moiety, and to preparation of such compounds. The invention also relates to pharmaceutical compositions and methods employing said compounds.

The compounds of the invention may be represented by the formula I:

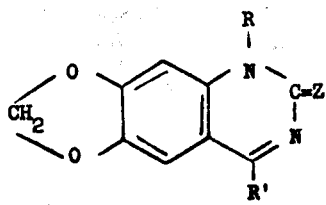

in which
Z is oxygen or sulfur,
R signifies an alkyl radical of 1 to 5 carbon atoms, e.g., methyl, ethyl, isopropyl and t-butyl; cyclo (lower)alkyl of 3 to 6 carbon atoms, e.g., cyclopropyl and cyclohexyl; or cyclo(lower)alkyl(lower) straight chain alkyl of 4 to 7 total carbon atoms in which the cycloalkyl is of 3 to 6 carbon atoms and the straight chain alkyl is of 1 to 3 carbon atoms, e.g., cyclopropylmethyl,
R' is

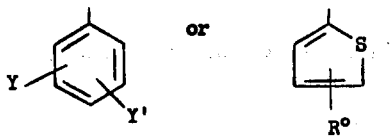

Y is hydrogen; halo of atomic weight of from 19 to 36, e.g., fluoro; lower alkyl of 1 to 3 carbon atoms, e.g., methyl; lower alkoxy of 1 to 3 carbon atoms, e.g., methoxy; nitro; or trifluoromethyl;
Y' is hydrogen; halo of atomic weight of from 19 to 36; lower alkyl of 1 to 3 carbon atoms; or lower alkoxy of 1 to 3 carbon atoms; or
Y and Y' together form methylenedioxy; and
R° is hydrogen; halo of atomic weight of from 19 to 36, e.g., chloro; or lower alkyl of 1 to 3 carbon atoms, e.g., methyl.

The compounds of formula I may be prepared by subjecting a corresponding compound of formula II:

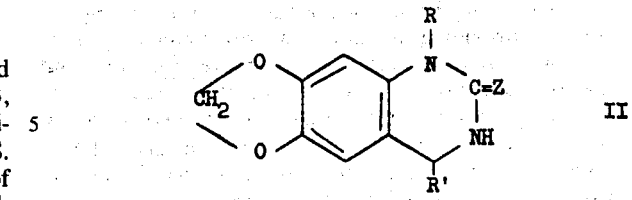

in which R and R' are as defined, to oxidation in an organic solvent.

The preparation of compounds I from compounds II by oxidation may be conveniently carried out in an inert organic solvent at temperatures in the range of 0°C. to 120°C., typically 15°C. to 100°C., where Z is oxygen and 20°C. to 60°C. where Z is sulfur. The oxidizing agents which may be employed are of known type suitable for converting an organic amino moiety to an imino moiety. Representative of such oxidizing agents are the alkali metal permanganates, such as sodium or potassium permanganate, manganese dioxide and mercuric acetate. The permanganates are the preferred oxidizing agents for producing the quinazolinones, while manganese dioxide, maintained essentially free of water, is the preferred oxidizing agent for making the quinazolinthiones. The organic solvent may be any of several conventional organic solvents including by way of illustration methylene chloride, the lower alkanols, e.g., methanol and ethanol, the aromatic solvents, e.g., benzene and the ethers including the cyclic ethers, e.g., dioxane. The product of formula I may be isolated from the reaction by working up by established procedures.

The compounds of formula II may be prepared by reacting an N-alkyl-N-(3,4-methylenedioxyphenyl)urea or thiourea of formula III:

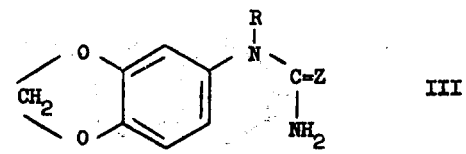

with a compound of the formula IV:

R'CHO  IV wherein Z, R and R' are as defined, at elevated temperatures whereby compounds of the formula II are obtained.

The reaction of compound III with compound IV is carried out at elevated temperatures in the range of 30°C. to 120°C., preferably 50°C. to 100°C. The reaction is suitably carried out in the presence of an acid as catalyst and dehydrating agent which is otherwise nonreactive with compounds III and IV, for example, an inorganic mineral acid, such as hydrochloric acid (hydrogen chloride in an aromatic solvent) or an organic acid such as tri-fluoroacetic acid, oxalic acid or an arylsulfonic acid or an alkysulfonic acid such as benzenesulfonic acid, p-toluenesulfonic acid and methanesulfonic acid, preferably the latter. The amount of acid catalyst is desirably controlled at a minor amount not substantially exceeding about one molar equivalent based on the compound III, and is most preferably a minor catalytic amount between 0.005 to 0.5 molar equivalent based on the urea. The conducting of the reaction under anhydrous or nearly anhydrous conditions is important to obtaining effective results. The reaction is conveniently carried out in an organic solvent which may be any of several conventional organic solvents providing an inert reaction medium, preferably an aromatic solvent such as benzene toluene and the like. Depending upon known factors such as reaction temperature, etc. the reaction may take typically between 1 to 50 hours. The reaction product of formula II may be isolated from the reaction mixture by working up by established procedures.

We had postulated that the preparation of compounds II by reaction of compounds III and IV proceeds through an intermediate of the formula A:

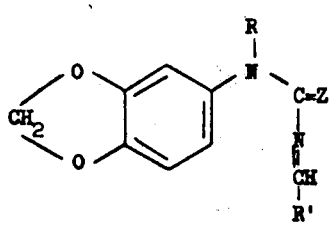

wherein Z, R and R' are as defined. In our experimentation conducted with reference to the more preferred embodiments of the invention it was evident that an intermediate of formula A had been formed on merely a transient basis, and that the reaction may directly produce compounds II in good yields in essentially a single stage operation when conducted under the preferred conditions as demonstrated, for example, in Step B of Example 1, hereinafter.

The urea compounds of formula III, i.e. those in which Z is oxygen, are preferably prepared by subjecting a compound of the formula V:

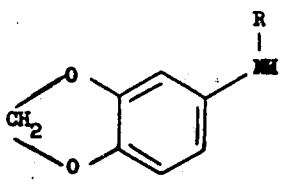

wherein R is as defined, to reaction with isocyanic acid which is provided in a conventional manner by forming in situ from an alkali metal isocyanate (also obtainable and known as alkali metal cyanates) and a suitable acid such as a lower aliphatic carboxylic acid, preferably acetic acid. The reaction may be suitably carried out at temperatures in the range of 10°C. to 50°C. and in an organic solvent medium which may be conveniently a lower aliphatic carboxylic acid such as excess acetic acid.

The urea compounds of formula III may also be provided starting with a compound of formula V by subjecting the latter to reaction with nitrourea at temperatures typically in the range of 80°C. to 120°C. in an inert organic solvent of conventional type, preferably a lower alkanol such as ethanol.

The compounds of formula III in which Z is sulfur may be suitably prepared by subjecting a compound of the formula VI:

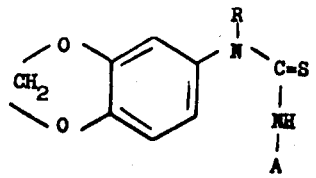

wherein R is as defined and A is the residue of an acid halide, to alkaline hydrolysis at elevated temperatures in the range of 50°C. to 140°C., preferably 80°C. to 120°C.

The hydrolysis is suitably effected employing an alkali metal hydroxide, preferably sodium or potassium hydroxide. The reaction is carried out in a suitable liquid solvent medium preferably comprising water and a water miscible inert organic solvent of conventional type such as an ether, including the cyclic ethers, preferably dioxane.

The reaction product of formula III may be isolated from the aforementioned reactions by working up by conventional procedures.

The compounds of formula V may be suitably prepared from known materials by established procedures. A preferred method of preparation of compounds V employs as starting material a compound of formula VII:

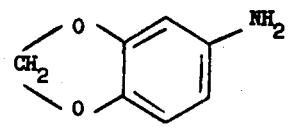

and involves subjecting said compound VII to known type protection reactions such as to reaction with a trialkylorthoformate followed by treatment with a strong acid such as sulfuric acid or to tosylation, alkylation and detosylation, all in a manner known per se. It will be noted that compounds V in which R is a cycloalkyl or branched alkyl with the branching occurring on the carbon atom attached to amino nitrogen, e.g., R is isopropyl, may be most conveniently and preferably prepared by reacting directly compound VII with the appropriate alkyl halide, as illustrated hereinafter in Step A of Example 1, in presence of an acid binding agent.

The compounds of the formula VI may be prepared by subjecting a compound of the formula V, above, to reaction with an isothiocyanate of formula VIII:

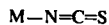

wherein M is a cation, and an acid halide of the formula IX:

wherein A is as previously indicated and X is halogen, preferably chloro, or to the action of the reaction product of said acid halide and isothiocyanate.

The preparation of compounds VI from a compound V is conveniently carried out in an inert solvent medium at temperatures in the range of 10°C. to 80°C., preferably 30°C. to 70°C. The reaction may be understood as including the reaction of compound V with the reaction product of the acid halide of formula IX and isothiocyanate of formula VIII. For this reason, it is generally preferred to first react the acid halide of formula IX and compound VIII and then add the starting compound V to the resulting reaction mixture. The reaction of the acid halide and isothiocyanate is preferably initiated at lower temperatures in the range of 10°C. to 40°C. As acid halides one employs any of the conventional acid halides which do not carry substituents or functional groups leading to undesired reactions. The more suitable materials are represented, for example, by acetyl chloride and benzoyl chloride, preferably benzoyl chloride. The preferred compounds VIII are those most readily reacting with the acid halide to eliminate as by-product a halide of the cation M. The preferred cations M may be represented, for example, by a cation of an alkali metal, e.g., sodium, and by the cation of ammonia, i.e., the ammonium salt. The more preferred compound VIII is ammonium isothiocyanate. Organic solvents suitable for the reaction are of conventional type which provide an inert medium. Such solvents include by way of example, benzene, the lower alcohols, ketones and cyclic ethers, preferably acetone. The reaction product of formula VI may be recovered from the reaction by working up by conventional procedures. It will also be noted that in going from compound V to compound III complete isolated and/or recovery of the intermediate compound VI is not necessary, and that in certain cases the reaction mixtures from the reaction of compounds V and VIII may contain varying amounts of the compound of formula III in which Z is sulfur.

The compound of formula VII can be prepared from known materials by established procedures, for example, by subjecting methylenedioxybenzene to nitration to obtain a 3,4-methylenedioxynitrobenzene which is then subjected to catalytic reduction with hydrogen employing a platinum oxide or palladium on charcoal as catalyst to obtain said compound of formula VII.

The compounds of formula I and also the intermediates of the formula II are useful because they possess pharmaceutical activity in animals. In particular, the compounds I and II are useful as anti-inflammatory agents as indicated by the Carrageenan-induced edema test in rats. For such use, the compounds may be combined with a pharmaceutically acceptable carrier, and such other conventional adjuvants as may be desired, and preferably administered orally in such forms as tablets, capsules, elixirs, suspensions and the like. For the above-mentioned use, the dosage administered will, of course, vary depending upon known factors such as the particular compound used and mode of administration. However, in general, the compounds of formula I in which Z is oxygen provide satisfactory results when administered at a daily dose of from about 0.15 milligrams to 180 milligrams per kilogram of body weight, preferably given in divided doses 2 to 4 times a day, with daily dosage for large mammals ranging from between about 10 milligrams to 1000 milligrams and individual doses between 3 milligrams to 500 milligrams. For the compounds of the formula I in which Z is sulfur satisfactory results are obtained at a daily dose of from 0.2 to 180 milligrams per kilogram of body weight with daily dosage for large mammals being between 16 to 1500 milligrams and divided doses between 4 and 750 milligrams. The compounds of formula II in which Z is oxygen in general provide satisfactory results when administered at a daily dose of from about 2 milligrams to 200 milligrams per kilogram of body weight, preferably given in divided doses, with daily dose for large mammals ranging between 140 milligrams to 2000 milligrams and individual doses ranging between 35 to 1000 milligrams. For the compounds of the formula II in which Z is sulfur satisfactory results are obtained at a daily dose of from 3 to 250 milligrams per kilogram of body weight with daily dosage for large mammals being between 200 to 2500 milligrams and divided doses between 50 and 1250 milligrams.

The compounds of the formulae I and II are also useful as analgesics as indicated by application of pressure to yeast-inflammed foot of the rat (oral administration). They are also useful as anti-pyretics as indicated by inhibition of yeast-induced fever in rats (oral administration). For such uses, the compound may be administered to obtain satisfactory results in modes and forms similar to those employed in the treatment of inflammation and at dosages indicated above as applicable for the use of the compound in the treatment of inflammation.

The intermediates of the formula III are also useful because they exhibit pharmacological activity in animals. In particular, the compounds of the formula III are useful as anti-inflammatory agents as indicated by the Carrageenan-induced edema test in rats. Such compounds, which may be administered in modes and forms similar to the compounds of formula I, generally provide satisfactory anti-inflammatory results when administered at a daily dose of from 2 to 200 milligrams per kilogram of animal body weight with daily dosage for large mammals being in the range between about 140 to 2000 milligrams and divided doses between 35 and 1000 milligrams.

For the above usage, oral administration with carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, favoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain the active ingredient admixed with an inert solid diluent, e.g. calcium carbonate, calcium phosphate and kaolin. The preferred pharmaceutical compositions from the standpoint of preparation and ease of administration are solid compositions, particularly solid diluent-filled capsules and tablets.

A representative individual dose form suitable for oral administration four times a day is a capsule prepared by conventional techniques and containing the following ingredients:

| Ingredient | Parts by Weight |
|---|---|
| 1-isopropyl-4-(p-fluorophenyl)-6,7-methylenedioxy-2(1H)-quinazolinone | 50 |
| Inert solid diluents: e.g. kaolin | 200 |

Preferred pharmaceutical compounds of the invention are those of formula I in which Z is oxygen and those in which R is isopropyl, more especially 1-isopropyl-4-phenyl-6,7-methylenedioxy-2(1H)-quinazolinone, 1-isopropyl-4(p-fluorophenyl)-6,7-methylenedioxy-2(1H)-quinazolinone, 1-isopropyl-4-(m-fluorophenyl)-6,7-methylenedioxy-2(1H)-quinazolinone and 1-isopropyl-4-phenyl-6,7-methylenedioxy-2(1H)-quinazolinthione.

The following examples are for purposes of illustration only.

EXAMPLE A

N-isopropyl-3,4-methylenedioxyaniline

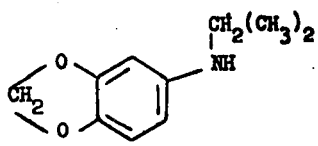

STEP A

Preparation of 1-nitro-3,4-methylenedioxybenzene

To 150 mls. of concentrated nitric acid cooled to and maintained at 0°C. is added 100 gms. of methylenedioxybenzene dropwise with vigorous stirring. At the end of the addition, the reaction mixture is diluted with several volumes of water, the precipitated solids collected by vacuum filtration and washed with several portions of water. Recrystallization of the crude solids from methanol provided 1-nitro-3,4-methylenedioxybenzene, m.p. 130°–141°C.

STEP B

Preparation of 1-amino-3,4-methylenedioxybenzene

To a solution of 38 gms. of 1-nitro-3,4-methylenedioxybenzene in 75 mls. of absolute ethanol is added 1.5 gms. of 5% palladium on carbon. The resulting mixture is hydrogenated at approximately 4 atmospheres pressure of hydrogen and ambient temperature for 4 hours. The catalyst is removed by filtration and the filtrate concentrated to a syrup. Trituration of the syrup with petroleum ether (b.p. 30°–60°C.) causes solidification and recrystallization from the same solvent provides 1-amino-3,4-methylenedioxybenzene, m.p. 37°C.

STEP C

Preparation of N-isopropyl-3,4-methylenedioxyaniline

To a solution of 197 gms. of 1-amino-3,4-methylenedioxybenzene in 1500 mls. of methanol is added 110.3 mls. of isopropyl iodide and 154.8 mls. of triethylamine. The resulting solution is refluxed for 32 hours at the end of which time the solvent is stripped at reduced pressure. The oil thus obtained is extracted repeatedly with diethyl ether. The extracts are combined, filtered through Celite, and the ether stripped off to obtain 1-isopropylamine-3,4-methylenedioxybenzene as an oil.

EXAMPLE 1

1-Isopropyl-4-phenyl-6,7-methylenedioxy-2(1H)-quinazolinone

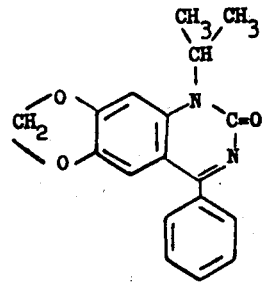

STEP A

Preparation of N-isopropyl-N-(3,4-methylenedioxyphenyl)urea

To a solution of 14.7 gm. of N-isopropyl-3,4-methylenedioxyaniline, prepared as in Example A, in 200 ml. of glacial acetic acid, cooled to 10°–18°C., is added 4.9 gm. of sodium isocyanate (sodium cyanate) in several portions. The resulting mixture is then stirred at ambient temperature for 15 hours. At the end of this time, the solvent is stripped at reduced pressure and the solid residue treated with 300 ml. of 2N sodium hydroxide. The resulting mixture is extracted with chloroform, dried and evaporated. The gum thus obtained is recrystallized from cyclohexane to obtain N-isopropyl-N-(3,4-methylenedioxyphenyl)urea, m.p. 116°–119°C.

STEP B

Preparation of 1-isopropyl-4-phenyl-6,7-methylenedioxy-3,4-dihydro-2(1H)-quinazolinone A solution of 10.3 gm. of N-isopropyl-(3,4-methylenedioxyphenyl)urea, 7.1 ml. of benzaldehyde, and 3 drops of methanesulphonic acid in 250 ml. of toluene is refluxed under a water separator for 21 hours. The cooled solution is then washed with 200 ml. of water, dried and evaporated to yield a powder. This product is decolorized in hot propanol with a small amount of activated charcoal and recrystallized from propanol to obtain 1-isopropyl-4-phenyl-6,7-methylenedioxy-3,4-dihydro-2(1H)-quinazolinone, m.p. 169°–172°C.

STEP C

Preparation of 1-isopropyl-4-phenyl-6,7-methylenedioxy-2(1H)-quinazolinone

To a solution of 8.5 gm. of 1-isopropyl-4-phenyl-6,7-methylenedioxy-3,4-dihydro-2(1H)-quinazolinone in 225 ml. of p-dioxane, cooled to 10°–13°C., is added dropwise a solution of 4.3 gm. of potassium permanganate in 185 ml. of water. When the addition is complete, 2 ml. of formalin solution are added. Precipitated solids are removed by filtration and the solvents stripped from the filtrate at reduced pressure. The residue is decolorized with activated charcoal in ethyl acetate and recrystallized from ethyl acetate to obtain 1-isopropyl-4-phenyl-6,7-methylenedioxy-2(1H)-quinazolinone, m.p. 187°–191°C.

EXAMPLE 2

1-Isopropyl-4-phenyl-6,7-methylenedioxy-2(1H)-quinazolinthione

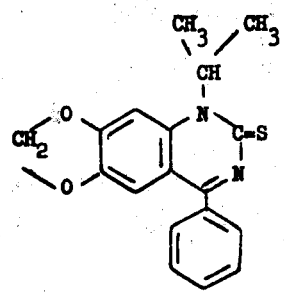

STEP A

Preparation of N-Isopropyl-N-(3,4-methylenedioxyphenyl)-N'-benzoyl thiourea

To a solution of 16.3 grams benzoyl isothiocyanate, prepared by refluxing 13.6 grams of dried sodium isothiocyanate with 17 grams of benzoyl chloride in 30 ml. of benzene, is slowly added, at room temperature, 28 grams of N-isopropyl-N-(3,4-methylenedioxyphenyl)-amine (prepared as in Example A) in 150 ml. benzene. The reaction mixture is stirred for 30 minutes at 20°C. and a solid forms which is recrystallized from benzene to yield N-isopropyl-N-(3,4-methylenedioxyphenyl)-N'-benzoyl thiourea melting at 152°–154°C.

STEP B

Preparation of N-Isopropyl-N-(3,4-methylenedioxyphenyl)-thiourea

To a stirred solution consisting of 45 ml. of dioxane and 200 ml. of water is added 27 grams of sodium hydroxide and the whole stirred until complete solution takes place. To this solution is added 17 grams of N-isopropyl-N-(3,4-methylenedioxyphenyl)-N'-benzoyl thiourea. The resulting mixture is heated to reflux for 48 hours and then cooled to 15°C. The resulting white solid is crystallized from benzene to obtain N-isopropyl-N-(3,4-methylenedioxyphenyl)-thiourea melting at 149°–151°C.

STEP C

Preparation of 1-isopropyl-4-phenyl-6-7-methylenedioxy-3,4-dihydro-2(1H)-quinazolinthione A solution of 30 grams of N-isopropyl-N-(3,4-methylenedioxyphenyl)thiourea, 27.6 mls. of benzaldehyde, and 2 mls. of methanesulphonic acid in 500 ml. of toluene is refluxed under a Dean Stark water separator for 4 hours, during which 2 ml. water is collected. The filtered solution is then evaporated to yield a powder. This product is recrystallized from dioxane and water to obtain 1-isopropyl-4-phenyl-6,7-methylenedioxy-3,4-dihydro-2(1H)-quinazolinthione, m.p. 215°–218°C.

STEP D

Preparation of 1-isopropyl-4-phenyl-6,7-methylenedioxy-2(1H)-quinazolinone

A mixture of 2 grams of 1-isopropyl-4-phenyl-6,7-methylenedioxy-3,4-dihydro-2(1H)-quinazolinthione, 100 ml. of methylene chloride and 4 grams of manganese dioxide is stirred for 48 hours at room temperature. Precipitated solids are removed by filtration and the filtrate evaporated to dryness. The residue is recrystallized from ethyl acetate and then methanol and then eluted with benzene in a silica gel column to give 1-isopropyl-4-phenyl-6,7-methylenedioxy-2(1H)-quinazolinthione, m.p. 202°–205°C.

EXAMPLE 3

Following substantially the procedure of Example 1 the following compounds of the invention are prepared:

A-1. 1-isopropyl-4-(m-fluorophenyl)-6,7-methylenedioxy-3,4-dihydro-2(1H)-quinazolinone, m.p. 165°–167°C.

A-2. 1-isopropyl-4-(m-fluorophenyl)-6,7-methylenedioxy-2(1H)-quinazolinone, m.p. 169°–170°C.

B-1. -isopropyl-4-(m-methoxyphenyl)-6,7-methylenedioxy-3,4-dihydro-2(1H)-quinazolinone, m.p. 167°–168°C.

B-2. 1-isopropyl-4-(m-methoxyphenyl)-6,7-methylenedioxy-2(1H)-quinazolinone, m.p. 189°–191°C.

C-1. 1-isopropyl-4-(p-methylphenyl)-6,7-methylenedioxy-3,4-dihydro-2(1H)-quinazolinone, m.p. 192°–194°C.

C-2. 1-isopropyl-4-(p-methylphenyl)-6,7-methylenedioxy-2(1H)-quinazolinone, m.p. 188°–190°C.

D-1. 1-isopropyl-4-(o-nitrophenyl)-6,7-methylenedioxy-3,4-dihydro-2(1H)-quinazolinone, m.p. 202°–205°C.

D-2. 1-isopropyl-4-(o-nitrophenyl)-6,7-methylenedioxy-2(1H)-quinazolinone, m.p. 148°–150°C.

E-1. 1-isopropyl-4-(5'-chloro-2-thienyl)-6,7-methylenedioxy-3,4-dihydro-2(1H)-quinazolinone, m.p. 162°–164°C.

E-2. 1-isopropyl-4-(5'-chloro-2-thienyl)-6,7-methylenedioxy-2(1H)-quinazolinone, m.p. 192°–201°C.

F-1. 1-isopropyl-4-(3,4-methylenedioxyphenyl)-6,7-methylenedioxy-3,4-dihydro-2(1H)-quinazolinone, m.p. 145°–147°C.

F-2. 1-isopropyl-4-(3,4-methylenedioxyphenyl)-6,7-methylenedioxy-2(1H)-quinazolinone, m.p. 234°–235°C.

G-1. 1-isopropyl-4-(m-nitrophenyl)-6,7-methylenedioxy-3,4-dihydro-2(1H)-quinazolinone, m.p. 218°–220°;

G-2. 1-isopropyl-4-(m-nitrophenyl)-6,7-methylenedioxy-2(1H)-quinazolinone, m.p. 230°–232°;

H-1. 1-isopropyl-4-(o-methylphenyl)-6,7-methylenedioxy-3,4-dihydro-2(1H)-quinazolinone, m.p. 172°–174°;

H-2. 1-isopropyl-4-(o-methylphenyl)-6,7-methylenedioxy-2(1H)-quinazolinone, m.p. 155°–157°;

I-1. 1-isopropyl-4-(p-fluorophenyl)-6,7-methylenedioxy-3,4-dihydro-2(1H)-quinazolinone, m.p. 163°–166°;

I-2. 1-isopropyl-4-(p-fluorophenyl)-6,7-methylenedioxy-2(1H)-quinazolinone, m.p. 238°–240°;

J-1. 1-isopropyl-4-(3,4-dichlorophenyl)-6,7-methylenedioxy-3,4-dihydro-2(1H)-quinazolinone, m.p. 155°–157°;

J-2. 1-isopropyl-4-(3,4-dichlorophenyl)-6,7-methylenedioxy-2(1H)-quinazolinone, m.p. 239°–242°;

K-1. 1-methyl-4-phenyl-6,7-methylenedioxy-3,4-dihydro-2(1H)-quinazolinone, m.p. 231°–232°;

K-2. 1-methyl-4-phenyl-6,7-methylenedioxy-2(1H)-quinazolinone, m.p. 257°–260°;

L-1. 1-cyclopropylmethyl-4-phenyl-6,7-methylenedioxy-3,4-dihydro-2(1H)-quinazolinone.

L-2. 1-cyclopropylmethyl-4-phenyl-6,7-methylenedioxy-2(1H)-quinazolinone.

EXAMPLE 4

Following substantially the procedure of Example 2 the following compounds of the invention are prepared:

A-1. 1-isopropyl-4-(m-fluorophenyl)-6,7-methylenedioxy-3,4-dihydro-2(1H)-quinazolinthione, m.p. 200°–203°C.

A-2. 1-isopropyl-4-(m-fluorophenyl)-6,7-methylenedioxy-2(1H)-quinazolinthione, m.p. 210°–214°C.

B-1. 1-isopropyl-4-(p-isopropylphenyl)-6,7-methylenedioxy-3,4-dihydro-2(1H)-quinazolinthione, m.p. 155°–157°C.

B-2. 1-isopropyl-4-(p-isopropylphenyl)-6,7-methylenedioxy-2(1H)-quinazolinthione, m.p. 167°–170°C.

C-1. 1-isopropyl-4-(p-fluorophenyl)-6,7-methylenedioxy-3,4-dihydro-2(1H)-quinazolinthione, m.p. 198°–199°C.

C-2. 1-isopropyl-4-(p-fluorophenyl)-6,7-methylenedioxy-2(1H)-quinazolinthione, m.p. 220°–223°C.

D-1. 1-isopropyl-4-(m-nitrophenyl)-6,7-methylenedioxy-3,4-dihydro-2(1H)-quinazolinthione, m.p. 115°–117°C.

D-2. 1-isopropyl-4-(m-nitrophenyl)-6,7-methylenedioxy-2(1H)-quinazolinthione, m.p. 199°–202°C.

What is claimed is:

1. A compound of the formula:

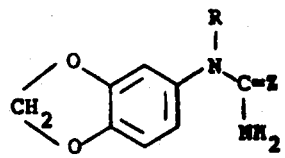

wherein
R is alkyl of 1 to 5 carbon atoms, cycloalkyl of 3 to 6 carbon atoms or cycloalkylalkyl of 4 to 7 total carbon atoms in which the cycloalkyl is of 3 to 6 carbon atoms and the alkyl is straight chain alkyl of 1 to 3 carbon atoms, and
Z is oxygen or sulfur.

2. A compound of claim 1 in which Z is oxygen.
3. The compound of claim 2 in which R is isopropyl.
4. A compound of claim 1 in which Z is sulfur.

* * * * *